(12) United States Patent
Sarangapani et al.

(10) Patent No.: US 7,445,799 B1
(45) Date of Patent: Nov. 4, 2008

(54) COMPOSITIONS FOR MICROBIAL AND CHEMICAL PROTECTION

(75) Inventors: Shantha Sarangapani, Walpole, MA (US); Quoc T. Truong, Hyde Park, MA (US)

(73) Assignee: ICET, Inc., Norwood, MA (US)

( * ) Notice: Subject to any disclaimer, the term of this patent is extended or adjusted under 35 U.S.C. 154(b) by 542 days.

(21) Appl. No.: 09/886,663

(22) Filed: Jun. 21, 2001

Related U.S. Application Data

(60) Provisional application No. 60/213,062, filed on Jun. 21, 2000.

(51) Int. Cl.
*A01N 25/12* (2006.01)
*A01N 25/34* (2006.01)
*A01N 55/02* (2006.01)
*A01N 59/00* (2006.01)
*A01N 59/16* (2006.01)
*A01N 59/20* (2006.01)

(52) U.S. Cl. ........................ 424/618; 424/404; 424/443; 424/486; 424/489; 424/619; 424/630; 424/631; 424/632; 424/633; 424/634; 424/635; 424/637; 424/638; 424/639; 424/641; 424/642; 424/646; 424/647; 424/648; 424/649; 514/184; 514/492; 514/494; 514/495; 514/499; 514/500; 514/502; 514/823; 514/974; 442/397; 428/411.1

(58) Field of Classification Search ................ 424/400, 424/402, 405–406, 409, 411, 443, 484–485, 424/489, 59, 617–618, 630, 639, 646, 404, 424/486, 619; 514/823, 974, 184, 495
See application file for complete search history.

(56) References Cited

U.S. PATENT DOCUMENTS

| | | | |
|---|---|---|---|
| 4,206,514 A * | 6/1980 | Yamauchi | 2/239 |
| 4,397,907 A | 8/1983 | Rosser et al. | |
| 4,513,047 A | 4/1985 | Leach et al. | |
| 5,003,638 A * | 4/1991 | Miyake et al. | 2/167 |
| 5,112,666 A | 5/1992 | Langston | |
| 5,221,572 A | 6/1993 | Meunier | |
| 5,391,426 A | 2/1995 | Wu | |
| 5,869,193 A | 2/1999 | Langley | |
| 6,013,275 A * | 1/2000 | Konagaya et al. | 424/443 |
| 6,037,281 A | 3/2000 | Mathis et al. | |
| 6,183,853 B1 | 2/2001 | Exsted | |
| 6,436,420 B1 | 8/2002 | Antelman | |
| 6,602,811 B1 | 8/2003 | Rock et al. | |
| 6,607,994 B2 | 8/2003 | Soane et al. | |
| 6,723,428 B1 * | 4/2004 | Foss et al. | 428/370 |
| 2002/0051823 A1 | 5/2002 | Yan et al. | |
| 2002/0192386 A1 | 12/2002 | Green et al. | |
| 2003/0013369 A1 | 1/2003 | Soane et al. | |
| 2003/0017194 A1 | 1/2003 | Joerger et al. | |
| 2003/0089136 A1 | 5/2003 | Lynch et al. | |
| 2003/1031635 | 7/2003 | Lynch et al. | |
| 2003/0157147 A1 | 8/2003 | Hoge et al. | |
| 2003/0190651 A1 | 10/2003 | Yan et al. | |
| 2003/0204916 A1 | 11/2003 | Green et al. | |

FOREIGN PATENT DOCUMENTS

WO  WO 01/27368  4/2001

OTHER PUBLICATIONS

The Encyclopedia of Chemistry, Van Nostrand Reinhold Co., New York, 3rd ed., 1974, p. 294, left column, see "Laminar Composites".*
Bradley, David, "Antibacterial Clothes", The Alchemist (The Chemweb Magazine) http://www.chemweb.com/alchemist, Jun. 24, 2003.

* cited by examiner

*Primary Examiner*—John Pak
(74) *Attorney, Agent, or Firm*—Weingarten, Schurgin, Gagnebin & Lebovici LLP

(57) ABSTRACT

An antimicrobial and chemical deactivating composition for use in a liquid medium or for incorporation into a coating, structural plastic materials, thin microporous membranes, textiles and sponges. The composition includes macrosize or submicron particles of silver, platinum with silver and their salts with parabens, oxide, salicylate, acetate, citrate, benzoate and phosphate along with copper and zinc salts of the same.

10 Claims, 2 Drawing Sheets

COMPOSITIONS FOR MICROBIAL AND CHEMICAL PROTECTION

Figure 1:
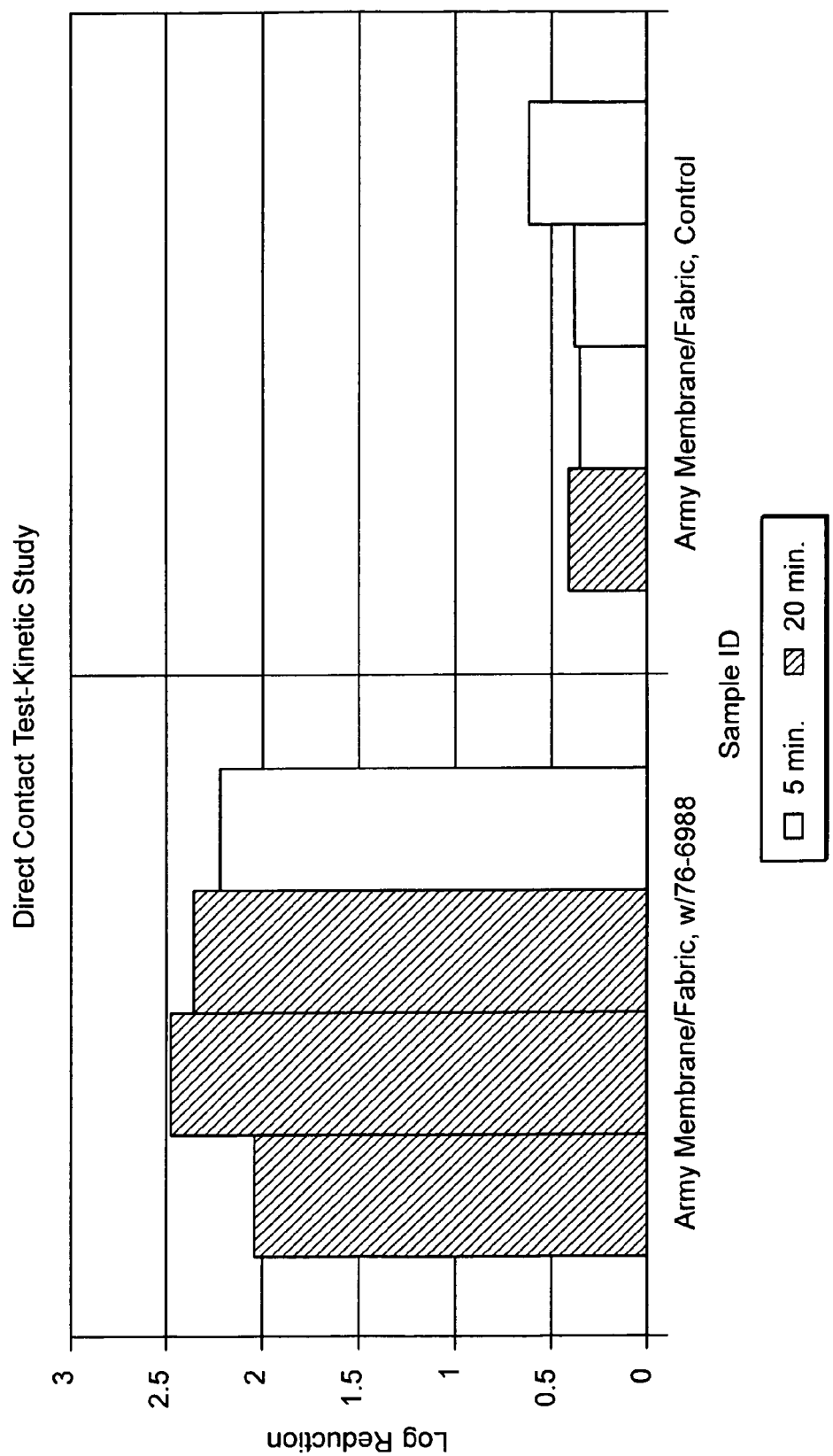
Figure 2:
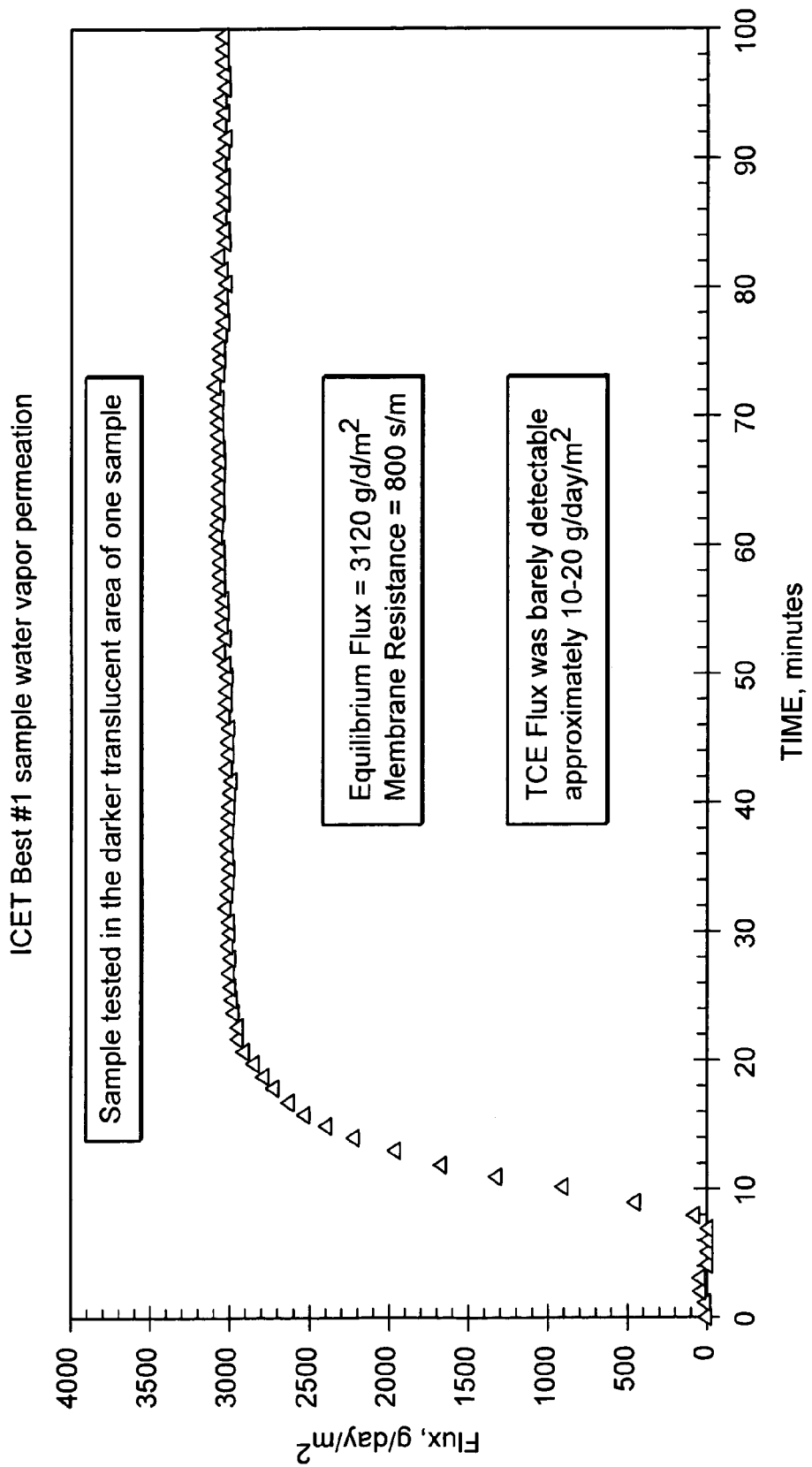

Certain inventions claimed in this application resulted partly from work done under the SBIR contract # DAAD16-00-C-9256 and SBIR contract # DAAK60-94-C-0025 from the Department of Defense (Army).

This application claims the benefit of Provisional Application 60/213,062, filed on Jun. 21, 2000.

BACKGROUND OF THE INVENTION

This invention relates to chemical formulations that can be incorporated into various materials in order to impart antimicrobial and chemical deactivating properties to the surfaces. Exposure to chemical and biological warfare agents (CBW) is of great concern to the soldiers and civilians as they could be totally vulnerable to such unexpected events. (Chemical Engineering News, July 1999). The various agents that could have a devastating effect on the population as well as the attending medical personnel. Even if the person's skin and face are protected, adsorption of the CBW agents could occur on their masks and clothing which may tend to linger on the surfaces leading to dangerous contamination of their surroundings as well as any open wounds or scratches. It is therefore extremely important that the clothing the soldiers or civilians wear have contact biocidal activity against the live BW (Biological warfare) agents and catalytic activity to destroy the CW (Chemical warfare) agents as well. Such clothing should be light with a high moisture vapor permeation rate and impermeable to the CBW agents.

Extensive non-military applications of this invention which can be incorporated into variety of special fabrics, offering an invisible shield against toxic vapors and germs are imminent. Examples are tents, boots, socks, paper-towels, sponges, respirators; hospital masks, sheets, garments for HAZ-Mat operations, and suits.

While activated carbon has been used in several of these applications, the carbon tends to retain the toxic ingredients or organisms and therefore is not desirable. A carbon-free "in situ" deactivating materials for suits for chemical and biological warfare agents is of great value to our nation.

Chemical weapons can be delivered as solids, liquids, vapors or aerosols by every major weapon system. They are classified by their duration and by their relationship to physiological effects. The barrier effectiveness of particular clothing to a particular chemical/mixture is dependent on the specific interactions between the clothing and the chemical/mixture. This is in turn is determined by the formulation of the clothing material, its method of manufacture, and its thickness. Temperature and other conditions can also influence the interactions. The key parameters that are of concern are The solubility of the chemical/aerosol mixture in the clothing material The breakthrough time of the chemical/aerosol for the material The permeation rate of the chemical/aerosol through the material.

Solubility is the weight of material absorbed by a known weight of material. In general chemicals having solubilities >10% rapidly permeate the rubber or the plastic. Many systems developed for food packing consist of multiple polymer layers where individual layers act as barriers to different permeants. These will include gas barriers, oil barriers, adhesive layers and printable layers. The CBW problem is more difficult in that good barrier polymers are often stiff, where as a flexible material is desired. Also elastomers tend to have weak internal bonding and so are naturally compatible with, and permeable to, organics. Likewise most elastomers will be less permeable to water than to organics. Finally, good moisture permeability implies some water swelling and so a significant change in properties with changes in humidity.

Permeation is expressed as a product of the diffusion coefficient and solubility of the permeant in the given polymer $P=D.S.$ Also, while D can be correlated with molecular size quite well, S varies enormously depending upon the solubility parameter of the molecule.

Biological weapons delivered in the form of aerosols are more long lasting than the chemical weapons and can propagate and infect the victims very quickly.

Biocidal agents can affect bacterial cells in a variety of ways:
  Protein coagulation. Most of the proteins in the bacterial cell are enzymatic, and exist in a finely dispersed state within the cell. Disinfecting chemicals such as heavy metals that cause these proteins to precipitate and coagulate make the cell non-functional and cause it to die.
  Disruption of cell membrane. The cell membrane acts as a selective barrier, allowing some solutions to pass through and other to be adsorbed onto the cell wall. Substances that concentrate at the cell membrane may alter the physical and chemical properties of the membrane, preventing its normal function. This may result in inhibition or death of the cell.
  Removal of free sulphydryl groups. Many of the enzyme proteins in a cell contain cysteine (an amino acid) and have side chains terminating in sulphydryl groups. These enzymes cannot function unless the sulphydryl groups remain free and reduced. If the sulphydryl groups are tied down—for example, by an oxidizing agent such as chlorine or heavy metals—wide spread damage to the cell occurs, and death may result.
  Enzymes and antibiotics perform their function through their affinity for specific chemical compounds normally found within cells, referred to as their "natural substrates." If a disinfecting compound structurally resembles a substrate in its essential aspects, the enzyme will have an affinity for that compound.

It is therefore the principal object of this invention is to provide chemical compositions that contain biocidal and catalytic properties for the "in situ" deactivation and destruction of biological and chemical agents respectively.

Another aspect of this invention is to provide formulations containing nanosize particles and carbon nanotubes that could potentially provide a very large surface area of contact.

Another aspect of the present invention is to provide these formulations for polymers, fibers and fabrics.

Yet another aspect of this present invention is to provide a laminating layer in the composite membrane that would allow water vapor to permeate while completely blocking organic vapors.

Another aspect of this invention is to provide a high surface area for this laminating polymer by cross-linking it on high area substrates such as carbon nanotubes, carbon black or nanophase oxides such as titanium oxide or such.

Another aspect of this present invention is to provide methodologies for incorporating the formulations from this invention in printing inks and shades during the printing of fabrics made from natural and/or synthetic fibers.

Another aspect of this present invention is to provide a finish coating incorporating the formulations from this invention, on a fabric or a surface.

Another aspect of this invention is to provide compositions for use with high area materials such as carbon fabric, felt, carbon blacks, carbon nanotubes and other high area materials for use in masks.

Yet another object of this invention is to provide a "triple defense" system where antimicrobials provide the biocidal actions, the catalytic materials provide chemical deactivation and the laminating layer provides a physical barrier to chemical vapors while allowing moisture.

BRIEF DESCRIPTION OF THE DRAWING

FIG. 1 is a graph showing the results of a direct contact test-kinetic study.

FIG. 2 is a graph showing the resistance to the permeation of trichloroethylene by a composite membrane.

DETAILED DESCRIPTION OF THE PREFERRED EMBODIMENT

In one aspect, the invention provides an antimicrobial, chemical protective and chemical agent deactivating material having a microporous polytetrafluoroethylene layer laminated to a continuous film of hydrophilic cross-linked polyvinylalcohol, a chemical deactivation component, and a biocidal component. The microporous polytetrafluoroethylene layer laminated to a continuous film of hydrophilic cross-linked polyvinylalcohol provides a physical barrier to chemical vapors, while permitting moisture to pass through the layer. The chemical deactivation component is free of activated carbon and is deposited on the polytetrafluoroethylene layer that is laminated to the cross-linked polyvinylalcohol film. The chemical deactivation component is dispersed within a carrier material. The chemical deactivation component includes an effective chemical deactivating amount of one or more chemically deactivating copper compounds, silver compounds, or elemental silver. The biocidal component is free of activated carbon and is deposited on the polytetrafluoroethylene layer that is laminated to the cross-linked polyvinylalcohol film. The biocidal component is dispersed within the carrier material. The biocidal component includes an effective biocidal amount of one or more biocidal copper compounds, silver compounds, or elemental silver. In the material, either the chemical deactivation component contains a chemically deactivating silver compound or elemental silver, or the biocidal component contains a biocidal silver compound or elemental silver.

In certain embodiments of the antimicrobial, chemical protective and chemical agent deactivating material, the chemical deactivation component includes a substance selected from the group consisting of nanosized cuprous or cupric oxide; a copper or silver complex of an imidazole, or an aminocarboxylic acid; micron or nanosized elemental silver or silver oxide; and a nanosized silver-copper alloy.

In certain embodiments of the antimicrobial, chemical protective and chemical agent deactivating material, the biocidal component includes a substance selected from the group consisting of silver phosphate, silver citrate, silver benzoate, silver salicylate, nanosized elemental silver, copper phosphate, copper acetate, copper salicylate, copper citrate, copper benzoate, nanosized silver-copper alloy, and nanosized cuprous or cupric oxide.

In still other embodiments of the antimicrobial, chemical protective and chemical agent deactivating material, the chemical deactivating component further includes, in addition to a copper compound, silver compound, or elemental silver, a substance selected from the group consisting of nanosized zinc oxide, nanosized molybdenum oxide, nanosized vanadium oxide, nanosized iron oxide, nanosized manganese oxide, titanium dioxide, carbon nanotubes, a tertiary amine, polyelectrolyte, polyvinylsulfonate, polyallylamine, elemental platinum, and platinum oxide.

In yet other embodiments of the antimicrobial, chemical protective and chemical agent deactivating material, the biocidal component further includes, in addition to a copper compound, silver compound, or elemental silver, a substance selected from the group consisting of zinc phosphate, zinc acetate, zinc salicylate, zinc citrate, zinc benzoate, zinc-1-hydroxypyridine-2-thione, nanosized zinc oxide, and bismuth subsalicylate.

Biocidal Components (Filler 1)

The submicron, micron or nanosize silver species are quite reactive toward the active chlorines of the agents and could render them inactive by converting the chlorines into silver chloride. The silver or silver ions are expected to be biocidal to microorganisms. Silver and some of its compounds is well known for its biocidal properties against a broad spectrum of microorganisms and its activity toward the labile chlorines of the agents is an added value in the material. Colloidal silver has been to be effective against 650 microorganisms including bacteria, virus and fungi. (Science Digest, March 1978). Unlike antibiotics, resistant strains have not shown to develop. Microscopic silver particles work as catalysts, disabling the enzyme used by the microorganisms for their oxygen metabolism.

Finely powdered silver phosphate, zinc phosphate and Bismuth subsalicylate are also useful biocidal combinations.

Finely powdered silver phosphate, silver citrate, silver benzoate, silver salicylate, zinc acetate, zinc salicylate and such from this invention are effective against spore forming bacteria such as *bacillus subtilis* a harmless surrogate of Anthrax and a host of other microorganisms.

Chemical Deactivation Components (Filler 2).

Nanosize oxides of copper (II), zinc, and molybdenum, vanadium and iron offer catalytic surfaces for the chemical agents to adsorb and become deactivated. Certain copper and silver complexes of biimidazole, imidazoles, aminocarboxylic acids are also included.

The addition of high area fillers such as carbon blacks, titanium di-oxide and/or carbon nanotubes to the formulations provide increased surface area.

The addition of a tertiary amine such as Dabco™ (Air Products and chemicals Inc. USA) helps the deactivation as well as the moisture permeation. The additions of polyelectrolytes such as polyvinylsulfonate (PolySciences, PA, USA) increase the moisture permeation.

High area carbon black such as M-1300 sold by Cabot Corporation contains—OH and COOH groups on its surface and allows chelation of metals.

Silver could be deposited on high area materials with and with out Platinum by using standard electroless reduction methods. Similarly the metal oxides will be coated use in sol-gel methods. Alternatively homogenized micron or nanosize size silver, silver oxide and metal oxides (Cerac Corporation, Nanophase Corporation) could be directly mixed with the resin, coating vehicles or dyestuff.

Platinum or platinum oxide is an excellent oxidizing agent for several organics. In very small catalytic quantities when dispersed as nanosized particles could deactivate certain toxic organic.

Physical barrier to organic and agents—Materials that exhibit excellent mechanical and moisture vapor permeation properties such as silicone rubber are found to be poor in terms of barrier properties. Most promising ones such as Teflon, FEP, etc exhibit poor elastomeric properties. A recent fluorocarbon elastomer advertised by DuPont-Dow called Kalrez has excellent chemical resistance but suffers from very poor moisture permeation properties and is also very expensive. Thin polymeric films of crosslinked polyvinylalcohol or fibers provide an effective barrier against a variety of toxic organic vapors. These polymers are easily processed. They form continuous films that are tough and flexible. These polymers can be directly heat bonded to a variety of substrates.

The best hydrophilic polymer known to man for excellent gas and organic barrier properties is a dry, protected film of polyvinylalcohol. The extensive hydrogen bonded structure is responsible for this behavior. Being crystalline the polymer film is brittle. The film is elasticized by a variety of materials such as glycerols. Being hydrophilic and elastomeric such layers will be quite moisture sensitive and will thus need to be a part of a multilayer structure to control exposure to water. The hydrophilic polymer is high molecular weight polyvinylalcohol cross linked with formaldehyde. Other variations include crosslinking with glyoxal or formaldehyde.

Heat bonding at about 200-250 C under a pressure of 80 pounds per square inch also allows thermal cross-linking.

By a combination of ethylene and vinyl alcohol a series of copolymers by the commercial name EVALs (EVALCO Corporation, ILL, USA) are available with superior processing properties. By blending or alloying these polymers can be further modified to yield barriers with gas barrier properties but which allow reasonable mass transport of water vapor.

A Chemical Barrier to Organic Vapors and Gases.

This invention has identified an important and potentially useful configuration. It is the possibility of creating an ion-pair complex between polycationic material such as polyallylamine hydrochloride and sodium polyvinyl sulfonate. This ion-pair complex is insoluble in water. Implementation of this configuration as a sandwich between thin layers hydrophilic polymers loaded with the deactivating fillers could prove to be a truly permselective barrier. Another configuration might involve bringing the two polymer layers containing the two ionic polymers and consecutively layering them in thin configurations. The additives such as polyvinylsulfonate and polyallylamine cation and their ion pair complex have a dramatic effect in reducing organic permeation while not affecting, some times, increasing the water permeation.

Chemical Deactivation Patterns.

Two types of agents are of interest: 1) "G" type nerve agents, and 2) mustards. Consider first the nerve agents, a P—F linkage is the reactive site for interaction with the serine hydroxyl of acetylcholinesterase, phosphorylating it and rendering it inactive. Destruction of the agent involves displacement of the fluoride by a nucleophile before it can reach the enzyme. This can be simply by reaction with water, which is relatively slow for the P—F compounds, thereby their ability to reach the enzyme, or facilitated by interaction with another nucleophile, such as a tertiary amine. The resultant species is particularly reactive with water and leads to the inactivation of the agent.

Similarly Mustards agents will deactivate by water attack or by the removal of the labile chlorines by the silver ions and silver. Several agents contain active chlorines that make the silver based approach attractive in combination with moisture transmitting fillers and their hydrophilic surface modifiers. Deactivation of chemical agents in the active layer will occur by hydrolysis. Similarly, destruction of the mustard agents can occur simply by water attack, or facilitated by initial faster) attack by a better nucleophile (tertiary amine) followed by water destruction of the intermediate species.

Matrix materials for the incorporation of the above fillers. A variety of plastic resins such as Kratons, hydrophilic polyurethanes, polyurethane—Teflon, polyalkenes, PVC, silicones, C-Flex, nylon or cellulose can be used for the incorporation of the fillers from this invention for a broad spectrum of applications. For the chemical protective suits, however, moisture vapor permeation is extremely important. For a good comfort level a permeation rate of at least 1000-200 gms. M2/day is desirable.

Incorporation of Fillers Into Printing Dyes and Into Finish Coating.

Nanoparticles contained in both water- and solvent-based coatings are easily wicked into a variety of fabrics including 50/50 nylon/cotton and triblend materials. Very low surface concentrations 0.1-0.2 mg/cm$^2$. These particles have volumes of approximately 800 cubic nanometers and surface areas of 500-600 square nanometers or approximately $10^{34}$ square nanometers of surface area per milligram of silver. By comparison, particles having the same geometry with dimensions in micrometers would yield approximately $10^{22}$ square nanometers of surface area per milligram of silver The active species of the metallic particles diffuse or "bloom" to the surface continuously. Reservoirs of biocidal and catalytic sites exist in the clothing materials that continuously migrate to the surface of the print or coating.

EXAMPLE I

This example illustrates the excellent barrier effects of very thin coatings of cross-linked polyvinylalcohol and fluorocarbon to ward actual chemical warfare agents. (Experiments carried out by Geomet Technologies, Gaithersburg, Md.). The notations "leak" and "adjacent cell" found in the table refers to leaks occurring through the rubber washer of the diffusion cell. According to Geomet, the leak is apparently caused by the poor sealing between the sample and washer in some cases and due to the attack of the sealing by the diesel in those tests where fuel resistance was tested. It required that such coatings maintain the barrier properties even after exposure to diesel. Also the leak affected the adjacent cell's color test paper as revealed from the color pattern developed. According to Geomet, these samples would have taken longer time to reach end points, if the leak had not occurred.

The cross-linked PVA coatings even after 10-minute exposure to diesel gave improvements of 200-1000% in permeation times for HD agents. For the GB agents increases in permeation time of 30-250% was noted on PVA (crosslinked) on viton rubber. It is surprising that the fluorocarbon did not show any improvement; micro defects were probably responsible. It passed all the simulant studies.

Bonding a thin coating to natural rubber, butyl rubber, nitrile rubber and Viton glove materials was tested for the purpose of reducing the transmission rates of CW agents.

Several solution phases' chemical grafting techniques were investigated to form thin barrier coatings. These included polyurethane, fluorocarbon, a hydrophilic polymer, silanes and silicone polymer coatings.

The data obtained are shown in Table I. Note the longer times for the break through for some coatings such as the hydrophilic polymer-polyvinylalcohol cross-linked form and the fluorocarbons. Please note that these results apply to surface modifications for certain rubbers used for glove making. There is no biocidal component here.

TABLE I

Our results on the various surface modifications of elastomers.
Static Diffusion Test Results (conducted at GeoMet Inc., MD)

| Sample Identification | | Type | Run # | Observed Endpoint (min) |
|---|---|---|---|---|
| HD SAMPLES | | | | |
| 027-076-01 | Butyl | Control | IID Run #1 | 565 |
| 027-076-01 | Butyl | Control | IID Run #1 | 595 |
| 027-076-01 | Butyl | Control | IID Run #1 | 625 |
| 027-076-02 | Butyl, Diesel Exposed | Control | IID Run #1 | 295 |
| 027-076-02 | Butyl, Diesel Exposed | Control | IID Run #1 | 250 |
| 027-076-02 | Butyl, Diesel Exposed | Control | IID Run #1 | 385 |
| 027-076-03 | Natural | Control | IID Run #2 | 185 |
| 027-076-03 | Natural | Control | IID Run #2 | 170 |
| 027-076-03 | Natural | Control | IID Run #2 | 170 |
| 027-076-04 | Neoprene | Control | IID Run #2 | 180 |
| 027-076-04 | Neoprene | Control | IID Run #2 | 130 |
| 027-076-04 | Neoprene | Control | IID Run #2 | 150 |
| 027-076-05 | Nitrile | Control | IID Run #2 | 120 |
| 027-076-05 | Nitrile | Control | IID Run #2 | 125 |
| 027-076-05 | Nitrile | Control | IID Run #2 | 120 |
| 027-076-06 | Silicone | Control | IID Run #2 | <5 |
| 027-076-06 | Silicone | Control | IID Run #2 | <5 |
| 027-076-06 | Silicone | Control | IID Run #2 | <5 |
| 027-076-14 | Natural | FC Coated | IID Run #2 | 305 |
| 027-076-14 | Natural | FC Coated | IID Run #2 | >2410 |
| 027-076-14 | Natural | FC Coated | IID Run #2 | >2410 |
| 027-076-15 | Neoprene | FC Coated | IID Run #2 | 400 |
| 027-076-15 | Neoprene | FC Coated | IID Run #2 | 290 |
| 027-076-15 | Neoprene | FC Coated | IID Run #2 | 290 |
| 027-076-16 | Nitrile | FC Coated | IID Run #2 | 230 |
| 027-076-16 | Nitrile | FC Coated | IID Run #2 | 260 |
| 027-076-16 | Nitrile | FC Coated | IID Run #2 | 2190 |
| 027-076-17 | Silicone | FC Coated | IID Run #2 | 55 |
| 027-016-17 | Silicone | FC Coated | IID Run #2 | 45 |
| 027-076-17 | Silicone | FC Coated | IID Run #2 | 55 |
| 027-076-08 | Butyl | RF Plasma Treated | IID Run #1 | 870 |
| 027-076-08 | Butyl | RF Plasma Treated | IID Run #1 | 765 |
| 027-076-08 | Butyl | RF Plasma Treated | IID Run #1 | 555 |
| 027-076-09 | Butyl | PVA Coated | IID Run #1 | 1985 |
| 027-076-09 | Butyl | PVA Coated | IID Run #1 | 1870 |
| 027-076-09 | Butyl | PVA Coated | IID Run #1 | 1590 |
| 027-076-12 | Butyl, *Adjacent to IID leak | FC Coated | IID Run #1 | 555 |
| 027-076-12 | Butyl, *IID leaked | FC Coated | IID Run #1 | 375 |
| 027-076-12 | Butyl | FC Coated | IID Run #1 | 1590 |
| 027-076-13 | Butyl | SARC | IID Run #1 | 870 |
| 027-076-13 | Butyl | SARC | IID Run #1 | 840 |
| 027-076-13 | Butyl | SARC | IID Run #1 | 760 |
| 027-076-10 | Butyl, Diesel Exposed **Adj. | PVA Coated | IID Run #1 | 975 |
| 027-076-10 | Butyl, Diesel Exposed **L | PVA Coated | IID Run #1 | 500 |
| 027-076-10 | Butyl, Diesel Exposed | PVA Coated | IID Run #1 | >2410 |
| 027-076-11 | Butyl, Diesel Exposed | FC Coated | IID Run #1 | 850 |
| 027-076-11 | Butyl, Diesel Exposed **L | FC Coated | IID Run #1 | 385 |
| 027-076-11 | Butyl, Diesel Exposed | FC Coated | IID Run #1 | 365 |
| GB SAMPLES | | | | |
| 027-076-07 | Viton | Control | GB Run #1 | 235 |
| 027-076-07 | Viton | Control | GB Run #1 | 235 |
| 027-076-07 | Viton | Control | GB Run #1 | 235 |
| 027-076-18 | Viton | FC Coated | GB Run #1 | 235 |
| 027-076-18 | Viton | FC Coated | GB Run #1 | 235 |
| 027-076-18 | Viton | FC Coated | GB Run #1 | 235 |
| 027-076-19 | Viton | PVA Coated | GB Run #1 | 825 |

TABLE I-continued

Our results on the various surface modifications of elastomers.
Static Diffusion Test Results (conducted at GeoMet Inc., MD)

| Sample Identification | Type | Run # | Observed Endpoint (min) |
|---|---|---|---|
| 027-076-19 Viton | PVA Coated | GB Run #1 | 415 |
| 027-076-19 Viton | PVA Coated | GB Run #1 | 305 |

FC = fluorocarbon; PVA = polyvinyl alcohol; SARC = silicone abrasion resistant coating. All PVA, SARC and FC coated samples were post treated with RF plasma (air - 100-200 mTorr), medium power, 30 minutes.
Diesel Exposure = Diesel fuel applied with Q-tip. Samples stay in hood 10 minutes. Samples blotted dry and tested immediately.
*= In IID Run #1, some coated samples were difficult to keep sealed, due to the "slickness" of the coating. Sample ID "027-076-12" had an IID leak around the outside of the sample, generating an artificially shortened endpoint time for this sample and for the adjacent sample.
**= In IID Run #1, the diesel fuel "ate" the wax seal from around the felt washer. This resulted in some samples leaking IID around the outside of the sample, generating an artificially shortened endpoint time for the samples and for some adjacent samples (Adj. = Adjacent to leaking samples; L = Leaking sample).
Note: The samples in IID Run #2 were sealed with duct sealant, which resulted in no leakage during the tests.

EXAMPLE 2

This example describes the preparation of a hydrophilic polyurethane material with ethylene polyvinylalcohol component. The latter adds barrier properties to organics while the polyurethane component allows moisture vapor transmission.

Dissolution of Ethylene Vinyl Copolymer LC-E151A

This copolymer has a glass transition temperature of 49° C. Solubility of this copolymer in organic solvents will be more rapid above this temperature. Of these solvents, it was decided to use DMSO for the initial work. A solution of the LC-E151A was made up in DMSO as follows:

LC-E151A-10.0—grams pellets
DMSO (Spec Grade)—50.0 mL

The LC_E151A-DMSO was stirred in a closed container, with a thermocouple in the liquid phase, in a mineral oil bath. The temperature was raised slowly to 94-95° C. Complete dissolution required approximately 2.5 hours. Two separate master batches were made. In order to reduce the amount of DMSO used, 1-propanol and tetrahydrofuran were added to separate portions of the master batch, with mixing, at room temperature (32° C.). The master batch (0.17 g/ml) tolerated greater than a tenfold addition (50 ml 1-propanol to 5 ml master batch). The master batch tolerated a fourfold addition of THF (20 ml THF to 5 ml master batch) before precipitating the polymer. The additions were made in 1 ml portions of solvent dropwise with stirring.

Another series of experiments were run where attempts were made to form membranes from both LC-E151A and Hypol 2002 in the same solution. To accomplish this end, solutions of Hypol 2002 were made in THF and in DMSO as follows Hypol 2002—50 grams
THF—50 ml This gives a solution of a 0.53 g polymer per gram of solution.

Hypol 2002—50 grams
DMSO—50 ml

This gives a solution of 0.46 g polymer per gram of solution.

These solutions proved to be too concentrated and difficulty was experienced with the membrane solutions gelling when mixed, either in the mixing container or in the casting tray shortly after being poured. It was necessary, in all cases, to add the Hypol solution to the LC-E151A solution in small amounts with good mixing. The THF additions of Hypol 2002 were considerably more sensitive to gelling than the DMSO additions of Hypol 2002. All combinations of Hypol 2002/LC-E151A (90/10 to 10/90) produced gels. Gelling with Hypol 2002/THF could probably be avoided by using more dilute solutions of the Hypol by replacing a portion of the THF with DMSO.

Three membranes were made up where the LC-E151A was dissolved in DMSO (master batch) and the Hypol 2002 was separately dissolved in DMSO, as above. The master batch of LC-E151A was diluted to approximately 0.08 grams LC-E151A per ram of solution before adding the Hypol 2002. The DMSO/Hypol solution was added to the DMSO/LC-E151A solution dropwise with mixing in proportions to yield membranes having a dry film composition of 90/10, 80/20 and 70/30 Hypol 2002/LC-E151A. Because of the high relative humidity and temperature, the Hypol immediately reacted with the atmospheric moisture. As the Hypol 2002 reacted with atmospheric moisture, the Hypol 2002 became a solid and the LC-E151A precipitated from solution. As a result of these two actions, the DMSO was released from the polymers and puddled on the membrane surface. The DMSO was blotted from the membrane surfaces and the membranes were washed with water in order to remove additional DMSO. These membranes will be more porous than the same membranes cast in a dry environment, vacuum dried to remove the DMSO, and then allowed to react with atmospheric moisture.

The composition of the solutions, as a starting point, might be

Hypol 2002—50 grams
THF—25 milliliters
DMSO—50 milliliters

This composition gives a solution having a concentration of 0.49 grams Hypol 2002 per gram of solution.

LC-E151A—5 grams
DMSO—50 milliliters

This composition gives a solution having a concentration of 0.078 grams LC-E151A per gram of solution.

Add the Hypol 2002 solution to the LC-E151A solution in small amounts with adequate mixing. For membranes having a dry film mass of 2.5 grams (150 square centimeter Petri dish casting surface), the following proportions may be used to prepare a series of membranes for study:

| Dry Film Ratio Hypol 2002/LC-E151A | Grams* Hypol Solution | Grams* LC-E151A Solution |
|---|---|---|
| 90/10 | 4.59 | 3.21 |
| 80/20 | 4.08 | 6.41 |
| 70/30 | 3.57 | 9.62 |
| 60/40 | 3.06 | 12.82 |
| 50/50 | 2.55 | 16.03 |

*Computations based on the specific gravities for DMSO and THF being 1.19 and 0.89 respectively The last experiment run was to cast a membrane of the Hypol 2002 (in THF) onto a 20 micron sheet of LC-E151. This was accomplished by using a drawn-down gauge. The concentration of the Hypol 2002 solution was 0.25 gram per ml of THF and the area of the membrane approximately 300 square centimeters. The draw-down gauge was set at 15 mils wet, which should resulting a dry film approximately 3 mils thick. This value should be checked since there may have been THF evaporation prior to the drawing of the film The film was dried at room temperature overnight. The dried film of the Hypol 2002 appeared uniform and well adhered to the LC-E151 film. In order to create an interpenetrating effect, I suggest replacing 5 percent of the THF with DMSO.

EXAMPLE 3

This example describes the CBW protective components of composite that consists of a membrane (not more than 5 mils in thickness) forming the underlayer for nylon or nylon/cotton or cotton or polyester or the triblend (nylon/cotton/Kevlar). The fillers from this invention are added to the PTFE resin and membranes of 1-5 mils thickness of varying porosities could be extruded.

The Concept of a "Triple Defense" CBW Protective Clothing

Our model for a composite fabric consists of a CBW deactivating shell fabric which is made of Nylon/cotton or Nylon with an under layer of microporous expanded PTFE membrane containing potent CBW deactivating agents. The PTFE is laminated with the special hydrophilic cross-linked polyvinylalcohol layer that is impermeable to CBW agents but highly permeable to water vapor. The micropores of the PTFE membrane can be tailor made ranging from 0.1 micron to 1 micron. The loading level of the fillers is of the order of 1-2%.

Microporous membranes such as PTFE with varying pore sizes from 0.5 micron, 0.1 and 0.05 micron could be made and the incorporation our catalytic fillers during the production of these membranes. Thus an opportunity exists to incorporate the biocidal and chemical deactivating fillers into porous expanded fluoroelastomer.

The goal is toward the construction of protective clothing that will facilitate the on-site destruction of CBW agents. This involves catalytic sites in the outer fabric and in the membrane composite closely spaced, which will speed the hydrolysis (or other destruction) of the agents as they come in contact with the clothing surface. In addition, we are providing in the composite a layer that physically blocks the penetration of the agents. In the present invention, to breach the barrier, the agent must pass through a catalyst bed of extremely high local concentration of biocidal and catalytic sites with water present. It then has to pass through a hydrophilic region, which by its very nature does not allow permeation of organics except water.

The bacteria or virus must breach a region of high concentration of the silver/heavy metal oxides organic acids/amines based catalyst and our experience has shown that a contact time of a few minutes will achieve deactivation. The water insoluble catalyticibiocidal compounds are held on the surface of the fabric by the polymeric layer, the concentration of the catalytic agent is much higher than involved in the previous studies. Not only are the catalytic sites held closely together in a limited region of space, but the water associated about these closely-packed sites, while sufficient for hydrolysis, is in relatively low concentration compared with the solution studies. This creates an environment in which the effect of the catalyst species should be extremely high, facilitating strongly the hydrolysis of both sarin-type and mustard type CBW agents.

EXAMPLE 4

Formulation Compositions

Biocidal Filler 1. Nanosilver, nanosilver-copper alloy powder, (silver content 97%) Nanopowder Industries, Israel) nanosize cuprous or cupric oxide, nanosize zinc oxide, nanosize cuprous oxide, Ultrafine silver or Zinc or Copper or Bismuth phosphate, acetate, salicylate, citrate, benzoate.

Parabens particularly Butyl Paraben and Octyl paraben Nano size refers to 1-100 nm.

Chemical deactivating filler 2. Nanosize Iron oxides, nanosize Vandium and Molybdenum or Manganese oxides. Nanosilver and silver or copper compounds. The fillers could also be loaded or prepared on high area substrates such as carbon materials, Talc, blacks, carbon nanotubes and other high area substrates. (see Table II).

TABLE II

Composition of formulations added to membranes and fabric coatings.

| Filler ID | 76-69A | 76-69B | 76-69AA | 76-69BB | 76-108-01 | 76-114-01 |
|---|---|---|---|---|---|---|
| Silver phosphate | 22.5% | | | 0.73% | 17.4% | 17.4% |
| CuO (Nano) | 25% | | 23.25% | 5% | 10.3% | 10.3% |
| Ferric Oxide (Nano) | 12.5% | | | 12.5% | | |
| ZnO (nano) | 12.5% | 2% | 12.5% | 1% | 10.3% | 10.3% |
| Silver (nano or 1 micron) | 27.5% | 5% | 27.5% | 5% | 20.6% | 20.6% |
| Silver citrate | | 5% | 22.5% | 8% | 10.3% | 10.3% |
| Butylparaben | | 83% | | 80.2% | | |
| Copper(I)Oxide | | 5% | 1.75% | | | |

TABLE II-continued

Composition of formulations added to membranes and fabric coatings.

| Filler ID | 76-69A | 76-69B | 76-69AA | 76-69BB | 76-108-01 | 76-114-01 |
|---|---|---|---|---|---|---|
| Sodium salicylate | | | | | 10.3% | 10.3% |
| Sodium triphosphate | | | | | 5.2% | 5.1% |
| Copper(II) phthalocyanine | | | | | 5.2% | 5.1% |
| Zinc pyrithione(optional) | (0.2-3%) | 0.2-3% | 0.2-3% | 0.2-3% | 0.2-3% | 0.2-3% |
| Sodium tri-phosphate | | | | | 10.3% | 10.3% |

We have included Zinc pyrithione as one of the ingredients in the formulations. See table below. Zinc Pyrithione (Sigma-Aldrich, St Louis) is an EPA approved biocide. (see table below). Dabco™ a tertiary amine sold by Aldrich or Air Products Company can also be blended with the above formulations.

Note: We have found that the addition of zinc pyrithione both in the membrane composition as well as in the textile formulation imparts a synergistic effect on the biocidal activities.

This product is sold by Olin Corporation under the name Omadine and has been recently approved by the EPA.

EXAMPLE 5

This example illustrates the idea of incorporating nanosize formulations from this invention into conventional and special textile finishes and lubricants. Nanosilver (50-70 nm available from vacuum technologies, Japan) and nano size oxides of iron, copper and zinc etc (Nanophase Technologies, ILL, USA), silver and or zinc acetates, salicylates, citrate, benzoate etc. (Alfa Aesar, MA, Aldrich Company, USA)

Nanoformulated Coatings (as a Textile Finish).

The idea that the coating solution containing fillers 1 and 2 be applied and wicked into the fabric from the back non-inked side. These coating solutions may be water- or solvent-based and can be applied by conventional fabric coating apparatus and techniques. (Auralube 243 for example, Sybron Chemicals, CT) A series of fabric samples where the mass/coating-mass ratio of the coating is varied and the amount of the coating applied to the coating are varied for each ratio. It is anticipated that the mass of nanoparticle loading will be in the range of 100-500 milligrams of coating per square meter of fabric.

Percentage of Each Ingredient in the Textile Mixture (Fabric Coating)

Solucote 1068 (Solual Industries, Warwick R.I.) 96.7%

Zn 1-Hydroxypyridine-2-Thione 0.3%

ICET's powder 76-69BB or 69AA 3.03%

Dabco™ (optional) (1-3%)

(Aldrich Company, St Louis)

Procedure for Coating the Fabrics

Textiles finish preparation: Weighed 1.57 g of a formulation from table II. In a small beaker, 0.157 g of Zinc Salt of 1-Hydroxypyridine-2-Thione and 6 g of Toluene was mixed. The mixture was ultrasonically mixed for 10 minutes. Fifty grams of Solucote 1068 was then added. The mixture was stirred until a uniform dispersion resulted. The final volume was about 80 ml.

Four 8"×18" pieces of fabric were coated with each batch of prepared textile finish. Paper tapes and rubber belts were used to pull the fabric pieces taut. A flat aluminum plate was used as a doctor blade to coat a thin layer of the mixture on the fabric (About 20 ml of the mixture was used for each piece of fabric). The coated samples were then dried in the oven at 100 C for 3 minutes. The fabrics coated were typically nylon, nylon/cotton or polyester.

EXAMPLE 6

Composite PTFE Membrane Fabrications

This example illustrates the preparation of a composite membrane with a laminated barrier layer.

Polyvinylalcohol 99% hydrolyzed (Molweight: 85,000-200,000) was dissolved in hot water (7.5 g/50 ml). About 10 drops of 100% glycerin, or an appropriate plasticizer (such as Trimethylol propane trimethacrylate, Sartomer Co. Inc., Exton, Pa.) was added and mixed well, followed by the addition of crosslinking agents or other additives as required.

The paste was then applied on to PTFE films and allowed to dry for about 5 minutes at ambient temperature. The sandwiched PVA between two PTFE membranes was then pressed at 225 C for 10 minutes at about 80-pounds/square inch.

The nanoformulations from Tables II were blended successfully with PTFE and extruded into thin membranes, typically of 0.77-2 micron pore size and about 1.2 mil thickness. (DeWAL Industries, RI)

These PTFE films in turn were processed using a special laminating procedure that further incorporated ICET's formulations as a sandwich between two ePTFE membranes containing about 02-1% of one of the formulations from table II.

Procedure:

1. Two 8"×8" unmodified ePTFE or ePTFE containing 1% of a formulation from Table II (made by DeWAL Industries) membranes were placed on two 10 mil teflon fiber gaskets and taped on the edges to keep the membranes wrinkle free.

2. Gel preparation a. 7.5 of PVA (Aldrich company, St Louis) (Mw 85,000-146,000) was added to 50 ml of distilled water. The mixture was stirred and heated at 80 C until the PVA dissolved. While still stirring the mixture, the following were added:

1.0 g of powder from example
0.1 g of TiO2
0.4 g of Citric acid
0.5 g of Zn1-Hydroxypyridine-2-Thione
10 drops of plasticizer (plasticizer (such as Trimethylol propane trimethacrylate, Sartomer Co. Inc., Exton, Pa.)

The dispersion was made uniform by stirring. It was spread onto the membranes using a meir rod. The membranes were then dried in an oven at 50 C for 50 minutes. The membranes were pressed at 350 Lbs./in$^2$ for 3 minutes at 400 F, such that a sandwich layer was formed by the pVA bound formulation. Pressure was maintained while the sandwiched membranes were cooled to room temperature.

Percentage of Each Ingredient in the Gel Formulation

PVA (85,000-146,000) 57.7% plasticizer 23.08% powder 69AA or 69BB 7.69%

Zinc 1-Hydroxypyridine-2-Thione 3.84%

Silver/Copper 3.84%

Citric acid 3.08%

TiO2 0.77%

EXAMPLE 7

Bonding of the Composite Membrane to the Coated Fabric

This example illustrates the method by which the composite membrane from example 5 is bonded to the coated fabric from example 4.

The membrane is coated with 1-2% Hypol 2000 (Hampshire Chemicals) and simply pressed onto the fabric. Overnight cure resulted in a membrane bound fabric. The product is refereed to as membrane-fabric.

EXAMPLE 8

Barrier Materials in the Composite Membrane

Tertiary Amines, polyelectrolyte ion-pair complexes. (Polyvinyl sulfonate, Polyvinyphosphonates with polycationic polyelectrolytes such as polyallylamine acid salts.) Polyvinyl alcohol modifications, polyvinyl alcohol fibers, ethylene vinyl alcohol copolymers in polyurethanes, Polyvinyl butyrals.

One variation of the preparation of the barrier membranes could be to carry out the crosslinking of the water soluble polymers such as polyvinyl alcohol on or inside carbon nanotubes or in the pores of high area black or fibers. The carbon nanotubes offer a high strength and a very high surface area. A small amount of carbon nanotubes in their the laminating layer or in the pTFE layer could have dramatic effects in the performance of the total composite despite the current high cost of the carbon nanotube.

EXAMPLE 9

This example illustrates the idea of incorporating the nanosize formulations in printing dyes. The nanosize formulations and ultrafine powders of compounds such as silver phosphate, benzoate, citrate, salicylates and zinc or silver acetates could be dispersed in dispersants prior to mixing into the Nanoparticle Inks The nanoparticles (fillers 1 and 2) will be incorporated into the camouflage coating inks directly. The nanoformulations could be included in the dispersants that are commercially used such as Kendisperse™ (Ken-lac, Inc. MA) or Super Lube™ (BF Goodrich, Cleveland, Ohio USA) The optimum mass of nanoparticles which can be incorporated to maintain the rheological properties of each ink is in the range of 1-5%. W./V Further, uninked fabric could be coated with only one color ink (such as the ground shade). A final fabric will be printed using multiple ink.

EXAMPLE 10

The resulting composite membranes are then tested for permeation of simulants such trichlorethylene that is a very small molecule and a powerful and a highly volatile solvent. The US Army uses this as a simulant for mustard gas. The following figure illustrates the resistance to the permeation of trichloroethylene by such a composite membrane.

EXAMPLE 11

Microbiological Tests

Log Reduction Test:
Purpose: To determine in a quantitative manner the log reduction kill by contacting membrane and fabric as well as membrane-fabric samples with viable spore or bacteria.

Procedure
1. Samples were cut into disks the same size as agar plates (diameter=8.6 cm, area=58 cm$^2$).
2. Appropriate dilutions of *Bacillus subtilis* var. *Niger* spores in 100 uL were spread onto tryptic soy agar plates.
3. Samples were placed onto the agar in a sterile manner and in the appropriate orientation.
4. Contact between the fabric and the agar was ensured by putting glass plates and stainless steel washers on top of the fabric samples.
5. Samples were incubated for 48 hours at 30 C.
6. After incubation, colonies that had formed on the plate were counted.
7. Log reduction values were calculated by comparing the colonies present in blank control plates vs. test plates.

TABLE III

Observations of growth of *Bacillus* spores on contacting various samples from this invention.

| Sample ID | Orientation | Initial Spore Count Spread on Plate | Observed Growth After 48 Hours of Contact | Log Reduction |
|---|---|---|---|---|
| With Army Fabric Samples, area = 58 cm$^2$ | | | | |
| Control Fabric | Printed Side Facing Agar | 4.19 * 10$^6$ | Lawn | 0-1 |

TABLE III-continued

Observations of growth of Bacillus spores on contacting various samples from this invention.

| Sample ID | Orientation | Initial Spore Count Spread on Plate | Observed Growth After 48 Hours of Contact | Log Reduction |
|---|---|---|---|---|
| Control Fabric | Printed Side Facing Agar | $4.19 * 10^6$ | Lawn | 0-1 |
| Control Fabric | Printed Side Facing Agar | $4.19 * 10^4$ | TNTC | 0-1 |
| Control Fabric | Printed Side Facing Agar | $4.19 * 10^4$ | TNTC | 0-1 |
| Sample From Examples 4, 5, and 6 | Printed Side Facing Agar | $4.19 * 10^6$ | 0 | >6.6 |
| Sample From Examples 4, 5, and 6 | Printed Side Facing Agar | $4.19 * 10^6$ | ~100 | 4.6 |
| Sample From Examples 4, 5, and 6 | Printed Side Facing Agar | $4.19 * 10^4$ | 0 | >4.6 |
| Sample From Examples 4, 5, and 6 | Printed Side Facing Agar | $4.19 * 10^4$ | 2 | 4.3 |
| Polyester Fabric Samples, area = 58 cm² | | | | |
| Control Polyester | — | $4.19 * 10^6$ | Lawn | 0-1 |
| Control Polyester | — | $4.19 * 10^6$ | Lawn | 0-1 |
| Control Polyester | — | $4.19 * 10^4$ | TNTC | 0-1 |
| Control Polyester | — | $4.19 * 10^4$ | TNTC | 0-1 |
| Sample from Example 4 | Thin Coating Facing Agar | $4.19 * 10^6$ | 0 | >6.6 |
| Sample from Example 4 | Thin Coating Facing Agar | $4.19 * 10^6$ | 0 | >6.6 |
| Sample from Example 4 | Thin Coating Facing Agar | $4.19 * 10^4$ | 0 | >4.6 |
| Sample from Example 4 | Thin Coating Facing Agar | $4.19 * 10^4$ | 0 | >4.6 |
| With Army Fabric/Membrane Samples, area = 58 cm² | | | | |
| Control | Printed Side Facing Agar | $1.19 * 10^4$ | TNTC | — |
| Control | Unprinted Side Facing Agar | $1.19 * 10^4$ | >1000 | 0-1 |
| Sample from Example 6 | Membrane Facing Agar | $1.19 * 10^4$ | 0 | >4.1 |
| Sample from Example 6 | Fabric Facing Agar | $1.19 * 10^4$ | 0 | >4.1 |
| Sample from Example 6 | Membrane Facing Agar | $1.19 * 10^4$ | 0 | >4.1 |
| Sample from Example 6 | Fabric Facing Agar | $1.19 * 10^4$ | 0 | >4.1 |
| Sample from Example 6 | Printed Side Facing Agar | $1.19 * 10^4$ | ~750 | 1.2 |
| Sample from Example 6 | Unprinted Side Facing Agar | $1.19 * 10^4$ | 0 | >4.1 |
| Sample from Example 4 | Coated Side Facing Agar | $1.19 * 10^4$ | 0 | >4.1 |
| Sample from Example 4 | Uncoated Side Facing Agar | $1.19 * 10^4$ | 0 | >4.1 |
| Sample from Example 4 | — | $1.19 * 10^4$ | 0 | >4.1 |

EXAMPLE 12

This example illustrates the contact biocidal activities of certain silicone and polyurethane materials that were incorporated with 1-5% of the formulations from this invention.

The plastic samples containing the formulations from this invention were tested for their effect on contacting *Bacillus Subtilis* globigii ATCC 9372, and its spores *Bacillus* var. *niger* (Steris corporation, MI) The bacteria were cultured in nutrient broth and maintained on nutrient agar plates.

Direct contact method: In a typical experiment, triplicates of the control and sample membranes of 1 cm2 were sterilized with alcohol, dried and used 10 uL of 10^7 cfu/ml of the were be placed on each disc in triplicates and allowed to incubate for 15, 30, 6 hrs, 12 hrs and 24 hrs at 30 C The discs were then placed in a PBS

| Samplecode | After 20 minutes contact colonies/mL | After 20 minutes contact colonies/mL | After 24 hrs Colonies/mL | After 24 hrs Colonies/mL |
|---|---|---|---|---|
| O55-153A | 0 | 0 | 0 | 0 |
| Control disc | 23 | 29 | lawn | lawn |
| Control blank | 33 | 30 | lawn | lawn |
| O55-153A | 5 | 6 | 0 | 0 | solution containing 1% nutrient broth, (1% peptone broth for the spores) sonicated for 1 minute vortexed for 10 secs and the appropriate dilutions plated out. The discs remaining in the rest of the solution were incubated overnight and plated the next day.

EXAMPLE 13

Parallel Streak Method

Qualitative (Zone of Inhibition Type Tests)(Carried Out by ViroMed, MN)

The procedure for protocol 1a was obtained from AATCC Technical Manual, 1993, Method 147-1988. Protocol 1a is a quantitative determination of antibacterial activity in fabric/membrane samples.

*Bacillus Subtilis* spores were used as one of the test organism, they were produced by inoculating *Bacillus Subtilis* (ATCC #19659) in Soil Extract Nutrient Broth at 37 C for ~3 days. This would cause the organism top sporulate. Inoculum was prepared by combining 1.0 mL of the culture broth and 9.0 mL of filter sterilized reagent water in a sterile container and mixing. This mixture was heat shocked at 80° C. for 20 minutes to kill all vegetative cells leaving only the endospores.

The other test organism used was *Mycobacterium bovis*-BCG. From a stock culture on Medium 7H11, the organism was transferred into Modified Proskauer-Beck broth and incubated for 21-25 days at 35-37° C. After incubation, one mL of Polysorbate 80 was added to the suspension. The broth was transferred to a tissue grinder and ground thoroughly. The inoculum was prepared by combining 1 mL of the 24 hour culture broth with 9 mL of filter sterilized water.

Test membrane and fabric samples were cut into 2.5 cm×5.0 cm rectangles. Sample cutting was done in a sterile manner.

Using a 2 mm inoculating loop, one loopful of the diluted culture was transferred to the surface the appropriate agar medium by making five, 7.5 cm long parallel streaks 1 cm apart in the center of the plate without refilling the loop. The agar used was Blood agar plates (BAP). Using sterile forceps, the test specimen was gently pressed transversely perpendicular across the five inoculum streaks ensuring contact with the agar. A sterilized glass plates were placed over the sample to ensure good sample/agar contact. The sample plates were then incubated for 18-24 hours at 37° C.

Following incubation, the plates were visually examined for interruption of growth along the streaks of inoculum beneath the fabric and for a clear zone of inhibition beyond the fabric edge. If necessary, the subcultures were placed at 2-8° C. for up to three days prior to examination.

Representative subculture plates showing growth were subcultured, stained and/or biochemically assayed to confirm or rule out the presence of the test organism.

Tests were conducted to assure the purity of culture and sterility of the agar plates. A "streak plate for isolation" test was performed on the organism culture and following incubation examined in order to confirm the presence of a pure culture. The acceptance criterion for this study control is a pure culture demonstrating colony morphology typical of the test organism. A representative sample of the uninoculated subculture medium will be incubated and visually examined. The acceptance criterion for this study control is lack of growth.

The heat shocked test organism suspension will be appropriately plated to determine the initial suspensions population. Acceptance criterion is >1×10$^7$ CFU/mL.

This study is designed to examine the zone of inhibition of a test material after inoculating a subculture plate with a test organism. Results will be expressed as the average width of the zone of inhibition around the test specimen. Minimum zone of inhibition values do not exist to specify a "passing" or "failing" test material. To constitute acceptable antibacterial activity, there must be no bacterial colonies directly under the test substance in the contact area. The zone of inhibition length is determined by subtracting the width of the sample plus the clear zone from the width the sample divided by two.

| Test Substance Identification | Replicate # | Width of clear zone of inhibition(In millimeters) *Bacillus subtilis* (ATCC19659) |
|---|---|---|
| ICET # 76-134-02 | 1 | 7 |
|  | 2 | 7 |
|  | 3 | 6 |
| ICET #Control | 4 | 0* |
|  | 5 | 0* |
|  | 6 | 0* |

*Growth was observed at the edge of the test material. No zone of inhibition.

| Test substance Identification | Replicate # | Width of clear zone of inhibition (mm) *Mycobactrium bovis*-BCG (OT 105401) |
|---|---|---|
| 76-116-01 (Control fabric). | 1 | 0* |
|  | 2 | 0* |
|  | 3 | 0* |
| 76-116-04 (samples form example 4, 5 and 6) | 1 | NA |
|  | 2 | NA |
|  | 3 | NA |

-continued

| | | |
|---|---|---|
| 76-116-05 (samples from example 4, 5 and 6). | 1 | NA |
|  | 2 | 7** |
|  | 3 | NA |

*= Growth was observed at the edge of the test material. No zone of inhibition.
NA = No Growth was seen on the entire plate
**= Only one small colony appeared on the plate and was located 7 mm away from the test material Control Results The following results from controls confirmed study validity:

| Type of Control | Results |
|---|---|
| Purity | Pure |
| Viability Control | Growth |
| Medium Sterility Control | No Growth |
| Parallel streak Control | Good Heavy Growth |

EXAMPLE 14

This example describes the effect of the membrane bonded fabric materials towards a virulent strain of *Anthra bacillus*. (Carried out at the Edgewood Chemical and Biological Center at Maryland, US Dept of Defense).

The common step to both protocols will be to prepare, examine, and quantify spores of the non-virulent strain of *Bacillus anthracis*, NNR1 Δ1 (Plasmid-free). The spore preparation is heated for an appropriate period of time at 65° C. to rid the sample of vegetative cells. The sample is then examined under the microscope to confirm the absence of vegetative cells and the presence of refractile spores. The titer of spores will be determined following dilution plating of 100-μl of $10^{-7}$ to $10^{-1}$ diluted samples on NBA (nutrient-broth agar, DIFCO) plates in triplicate. The desired spore titer of the sample used is expected used is expected to be 1–2× $10^8$/ml suspension.

Protocol:

After pouring NBA plates, 100-μl of spore suspension containing different titers will be spread. The appropriately cut and sterilized fabric will be overlaid and sterile soft agar will be poured to prevent curling of the fabric. Colonies will be counted after 18-24 hours of incubation at 30° C. The number of cfu (colony forming units) on test plates will be compared to the controls detailed above. All the treatments will be done in triplicate, and the entire experiment will be repeated at least once to make a meaningful statistical conclusion.

The spore dilutions were made ranging from $10^{-1}$ to $10^{-5}$. An aliquot of 50·1 was plated, and the ICET material was placed directly over the spread spores. Since the fabric has a tendency to curl, two approaches to straighten the fabric were followed, one poured agar (0.7% prepared in water) or a glass weight supplied by ICET. It was easier to use the glass weight. The membrane itself did not curl, and therefore required no weight or poured agar. The control samples from ICET yielded the same results as no treatment as shown below. The stock spore titer was ~1.5×10$^8$/ml.

TABLE IV

| | Cfu | | | | | | | |
|---|---|---|---|---|---|---|---|---|
| | Control | | ICET #1 | | ICET #2 | | ICET #7 | |
| Dilution | Poured agar | Glass | Poured Agar | Glass | Poured Agar | Glass | Poured Agar | Glass |
| 10-1 dil. | TNTC* | TNTC | | | | | | |
| 10-2 dil. | " | " | | | | | | |
| 10-3 dil. | " | " | | | | | | |
| 10-4 dil. | 560 | 530 | | | | | | |
| 10-5 dil. | 78 | 72 | | | | | | |

* = too numerous to count.

In conclusion, none of the 30,000 spores survived in the presence of ICET material, when protocol A was followed.

EXAMPLE 15

The *bacillus* var *niger* spores (sterimed Corp, MI) are considered to be surrogates for Anthrax spores. This example illustrates the rate of the biocidal action of the membrane-fabrics form example 4, 5, 6 and 7 against the *Bacillus* spores.

Direct Contact Kinetic Study

The purpose of this test was to begin to determine the rate kinetic of biocidal activity of the ICET membrane/fabric.

Procedure:

One inch diameter fabric/membrane samples were cut and placed into the bottom of small sterile disposable tubes with the fabric side facing up in a cup shape.

A solution containing $10^5$ cfu/ml of *Bacillus Subtilis* var. *Niger* spores (ATCC# 9372) was prepared by diluting a spore suspension. The spore suspension was obtained from Steris Corp (Erie Pa.). The spore suspension contained $2.5*10^7$ cfu/0.1 ml of the spores, in a 40% ethanol solution. The dilution was done in sterile distilled water.

100 μL of the $10^5$ cfu/ml spore dilution was added to each tube. The solution quickly absorbed into the fabric. The tubes were capped and incubated at 30° C. for a set period of time (5 min. and 20 min.). After the incubation period, 1 ml of Phosphate buffered saline was added to each sample. Each sample tube was vortexed 1 minute. 10 μL samples from each tube were then taken and plated onto Tryptic Soy Agar Plates.

Results:

As can be seen in FIG. 1 below, significant biocidal activity is detected at both the 5 minute and 20 minute time points for the ICET modified Membrane/Fabric sample. The significant point of this result is that the ICET modified samples activity begin very quickly. Note that the challenge level was an inoculum of 10,000 spores/1" diameter swatch. Hence the 2.5 log reduction.

EXAMPLE 16

This example illustrates the performance of sponges containing certain formulations of the composition of the present invention. The polymer encapsulated antimicrobials provide longer life in spite of hundreds of washings. Such sponges could be of potential use during decontaminations as well as for consumer products.

Consumer sponges are currently made from hydro cellulose using the well known viscose process. The hydro cellulose is dispersed at a high pH at about 100° C. followed by a series of treatments with acid, neutralization, hypochlorite and washings etc.

The encapsulated formulation was prepared as follows:

A mixture of 90 grams of Butyl Paraben (Sigma-Aldrich, MO), 10 grams of silver powder (Cerac), 4.5 grams of silver salicylate (Alfa Aesar, MA) and 0.5 grams Copper Phthalocyanine (Sigma-Aldrich, MO) were finely ground and added to 50 ml of polyhydroxyethylmethacrylate, (phema) MW 300,000 (5% in ethanol) (Polysciences, PA). The paste was well stirred and allowed to form a uniform slurry. The excess alcohol was evaporated and then 100 mL of distilled water was added. The phema encapsulated powder precipitated immediately as a voluminous precipitate. This was filtered and dried at 60-80° C. for 2 days (labelled as 071-116A).

As an alternative encapsulant one may choose to use Aquazol™ (Polymer Innavations, AZ) or Guar Gum or cellulose or cross-linked PVA. The resulting material was powdered and incorporated at a 5% and 10% level during the sponge formation process. The resulting sponges were tested for antimicrobial activities.

Currently such sponges are post-treated with antimicrobials to prevent growth of microorganisms in the sponge matrix. This is an expensive process and more benign antimicrobials that are environmentally friendly have been sought.

Other Variations in the formulation include the incorporation of nanosize particles, zinc salts and silver salts such as phosphates, citrates, and benzoates.

Biocidal Activity of the Sponge.

The sponge samples were divided into three groups. (1) Unwashed (2) 100 times washed (3) 500 times washed.

A "wash" is defend as saturating the sponge with tap water followed by squeezing the water out of the sponge by hand.

The moist sponge pieces (29 mm disks) were directly inoculated with about 10,00 cells of each *Staph Aureus* and *E. Coli*. A control with the above organisms was prepared in a sterile tube. After 3-4 hours, 5 mL of 10% brain heart infusion broth in PBS was added to the tubes containing the sponges and the controls.

The tubes were incubated for two days after vortexing. On the third day the supernate was plated on Brian Heart Infusion Agar plates to check any growth of the sponge inoculated bacteria. The results are shown in the table below.

TABLE V

| Sample Type | # of Washes | Plate count after three days |
|---|---|---|
| 071-116A | 0 | 0 |
| | 100 | 0 |
| | 500 | 0 |
| Control, no sponge | — | Lawn(over several million cells) |

EXAMPLE 17

The compositions described in this invention could be successfully incorporated in electrospun nanofibers, a process in which polymers are drawn as nanofibers. (proceedings from "Nanotechnology for soldier system" conference, 1998 July, MA.).

EXAMPLE 18

Formulation Compositions

Biocidal Filler 1. Nanosilver, nanosilver-copper alloy powder, (silver content 97%) Nanopowder Industries, Israel) nanosize cuprous or cupric oxide, nanosize zinc oxide, nanosize cuprous oxide, Ultrafine silver or Zinc or Copper or Bismuth phosphate, acetate, salicylate, citrate, benzoate.

Parabens Particularly Butyl Paraben and Propyl Paraben

Nano size refers to 1-100 nm.

Chemical deactivating filler 2. Nanosize Iron oxides, nanosize Vandium and Molybdenum or Manganese oxides. Nanosilver and silver or copper compounds. The fillers could also be loaded or prepared on high area substrates such as carbon materials, Talc, blacks, carbon nanotubes and other high area substrates. A typical composition is shown in the table below.

TABLE

Composition of Biocidal Filler 1 and Chemical Deactivating Filler 2 added to membranes and fabric coatings.

| Composition | A | B |
|---|---|---|
| Silver phosphate | 1.4% | 1.4% |
| CuO (Nano) | 10.3% | 10.3% |
| Ferric Oxide (Nano) | 2% | 2% |
| ZnO (nano) | 1.3% | 1.3% |
| Silver (nano or 1 micron) | 2.6% | 2.6% |
| Silver citrate | 1.3% | 1.3% |
| Butylparaben | 45% | 45% |
| Dabco (tertiary amine). | | 5% |
| Silver salicylate | 1.3% | 1.3% |
| Silver phosphate | 5.2% | 5.1% |
| Copper(II) phthalocyanine | 2% | 2% |
| Zinc pyrithione(optional) | | 0.2-3% |
| Titanium di oxide (nano) | 10.3% | 10.3% |

We have included Zinc pyrithione as one of the ingredients in the formulations. See table below. Zinc Pyrithione (Sigma-Aldrich, St Louis) is an EPA approved biocide see table below).

Dabco™ a tertiary amine sold by Aldrich or Air Products Company can also be blended with the above formulations.

Note: We have found that the addition of zinc pyrithione both in the membrane composition as well as in the textile formulation imparts a synergistic effect on the biocidal activities.

This product is sold by Olin Corporation under the name Omadine and has been recently approved by the EPA.

Montmorrillonite is a type of Talc and can be used as well.

What is claimed is:

1. An antimicrobial, chemical protective and chemical agent deactivating material comprising:
    a microporous polytetrafluoroethylene layer laminated to a continuous film of hydrophilic cross-linked polyvinylalcohol for providing a physical barrier to chemical vapors while permitting moisture to pass through said layer;
    a chemical deactivation component free of activated carbon deposited on said polytetrafluoroethylene that is laminated to said cross-linked polyvinylalcohol, said chemical deactivation component being dispersed within a carrier material, said chemical deactivation component comprising an effective chemical deactivating amount of one or more chemically deactivating copper compounds, silver compounds, or elemental silver; and
    a biocidal component free of activated carbon deposited on said polytetrafluoroethylene that is laminated to said cross-linked polyvinylalcohol, said biocidal component being dispersed within said carrier material, and said biocidal component comprising an effective biocidal amount of one or more biocidal copper compounds, silver compounds, or elemental silver;
    wherein said chemical deactivation component contains a chemically deactivating silver compound or elemental silver, or said biocidal component contains a biocidal silver compound or elemental silver.

2. The antimicrobial, chemical protective and chemical agent deactivating material of claim 1, wherein said chemical deactivation component comprises a substance selected from the group consisting of nanosized cuprous or cupric oxide; a copper or silver complex of an imidazole, or an aminocarboxylic acid; micron or nanosized elemental silver or silver oxide; and a nanosized silver-copper alloy.

3. The antimicrobial, chemical protective and chemical agent deactivating material of claim 1, wherein said biocidal component comprises a substance selected from the group consisting of silver phosphate, silver citrate, silver benzoate, silver salicylate, nanosized elemental silver, copper phosphate, copper acetate, copper salicylate, copper citrate, copper benzoate, nanosized silver-copper alloy, and nanosized cuprous or cupric oxide.

4. The antimicrobial, chemical protective and chemical agent deactivating material of claim 1, wherein said chemical deactivation component further comprises a substance selected from the group consisting of nanosized zinc oxide, nanosized molybdenum oxide, nanosized vanadium oxide, nanosized iron oxide, nanosized manganese oxide, titanium dioxide, carbon nanotubes, a tertiary amine, polyelectrolyte, polyvinylsulfonate, polyallylamine, elemental platinum, and platinum oxide.

5. The antimicrobial, chemical protective and chemical agent deactivating material of claim 1, wherein said biocidal component further comprises a substance selected from the group consisting of zinc phosphate, zinc acetate, zinc salicylate, zinc citrate, zinc benzoate, zinc-1-hydroxypyridine-2-thione, nanosized zinc oxide, and bismuth subsalicylate.

6. The antimicrobial, chemical protective and chemical agent deactivating material of claim 1, wherein the polytetrafluoroethylene layer contains carbon nanotubes.

7. The antimicrobial, chemical protective and chemical agent deactivating material of claim 1, wherein the cross-linked polyvinylalcohol film contains carbon nanotubes.

8. The antimicrobial, chemical protective and chemical agent deactivating material of claim 1, wherein the cross-linked polyvinylalcohol film contains glycerin or a plasticizer.

9. The antimicrobial, chemical protective and chemical agent deactivating material of claim 8, wherein the plasticizer is trimethylol propane trimethacrylate.

10. The antimicrobial, chemical protective and chemical agent deactivating material of claim 1, further comprising a second microporous polytetrafluoroethylene layer laminated to said continuous film of hydrophilic cross-linked polyvinylalcohol.

* * * * *